United States Patent [19]

Tjoeng et al.

[11] Patent Number: 5,091,396

[45] Date of Patent: Feb. 25, 1992

[54] PYRIDYL PEPTIDE MIMETIC COMPOUNDS WHICH ARE USEFUL PLATELET-AGGREGATION INHIBITORS

[75] Inventors: Foe S. Tjoeng, Manchester; Steven P. Adams, St. Charles, both of Mo.; Robert B. Garland; Masateru Miyano, both of Northbrook, Ill.

[73] Assignees: Monsanto Co., St. Louis, Mo.; G. D. Searle & Co., Skokie, Ill.

[21] Appl. No.: 637,728

[22] Filed: Jan. 7, 1991

Related U.S. Application Data

[60] Division of Ser. No. 513,532, Apr. 23, 1990, Pat. No. 5,037,808, which is a continuation-in-part of Ser. No. 395,614, Aug. 8, 1989, abandoned, which is a division of Ser. No. 221,703, Jul. 20, 1988, Pat. No. 4,879,313.

[51] Int. Cl.$^5$ .................. A61K 31/44; C07D 213/02
[52] U.S. Cl. ........................... 514/357; 546/332
[58] Field of Search .................. 546/332; 514/357

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,879,237 | 11/1989 | Rouslahti et al. | 435/240.2 |

OTHER PUBLICATIONS

Kloczewiak et al., Biochem. 23, 1767–1774 (1984).
Plow et al, Proc. Natl. Acad. Sci. 82, 8057–8061 (1984).
Ruggeri et al, Ibid. 83, 5708–5712 (1986).
Ginsberg et al, J. Biol. Chem. 260(7), 3931–3936 (1985).
Haverstick et al., Blood 66(4) 946–952 (1985).

*Primary Examiner*—C. Warren Ivy
*Assistant Examiner*—Zinna Northington Davis
*Attorney, Agent, or Firm*—Scott J. Meyer; James W. Williams, Jr.

[57] ABSTRACT

Novel peptide mimetic compounds are provided which have useful activity as inhibitors of platelet aggregation. These compounds have the chemical structure

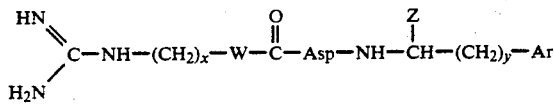

wherein
 x = 4 to 8,
 y = 0 to 4,
 W = $CH_2$—$CH_2$ or C≡CH,
 Z = H, COOH, $CONH_2$, $CH_2OH$, $CO_2R$, $CH_2OR$ or $C_{1-6}$ alkyl,
 R = $C_{1-6}$ alkyl,
 Ar = a nitrogen-containing heterocyclic group, and
 Asp = aspartic acid residue.

8 Claims, No Drawings

PYRIDYL PEPTIDE MIMETIC COMPOUNDS WHICH ARE USEFUL PLATELET-AGGREGATION INHIBITORS

CROSS REFERENCE TO RELATED APPLICATIONS

This is a division of application Ser. No. 07/513,532, filed Apr. 23, 1990 now U.S. Pat. No. 5,037,808 which is a continuation-in-part of application Ser. No. 07/395,614, filed Aug. 8, 1989, which in turn is a division of application Ser. No. 07/221,703, filed July 20, 1988, now U.S. Pat. No. 4,879,313.

BACKGROUND OF THE INVENTION

This invention relates to novel peptide mimetic compounds having activity as inhibitors of platelet aggregation.

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. These polypeptides include an internal amino acid sequence Arg-Gly-Asp-Ser. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517. These peptides were defined as X-Arg-Gly-Asp-R-Y wherein
X=H or amino acid,
R=Thr or Cys; and X-Arg-Gly-Asp-Ser-Y wherein
X=H or amino acid,
Y=OH or amino acid.

In U.S. Pat. No. 4,683,291, inhibition of platelet function is disclosed with synthetic peptides designed to be high affinity antagonists of fibrinogen binding to platelets. These synthetic peptides have up to 16 amino acid residues with Arg-Gly-Asp-Val or Arg-Gly-Asp-Ser at the C-terminal.

Similar synthetic peptides which contain the Arg-Gly-Asp sequence and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

In U.S. Pat. No. 4,857,508, certain novel tetrapeptide derivatives are disclosed which have enhanced activity as inhibitors of platelet aggregation. These tetrapeptide derivatives contain the sequence X-Gly-Asp-Y in which X and Y are defined to comprise a variety of organic moieties. An illustrative preferred example is Arg-Gly-Asp-(O-methyl-Tyr)-$NH_2$.

BRIEF DESCRIPTION OF THE INVENTION

In accordance with the present invention, novel peptide mimetic compounds are provided which have useful activity as inhibitors of platelet aggregation. They are believed to act by antagonizing interactions between fibrinogen and/or extracellular matrix proteins and the platelet gpIIb/IIIa receptor. The novel inhibitor compounds of this invention have a guanidino group at the N-terminus, a pseudopeptide or peptide mimetic bond in the chain and a nitrogen-containing heterocyclic group at the C-terminus. These peptide mimetic compounds can be represented by the following chemical structure:

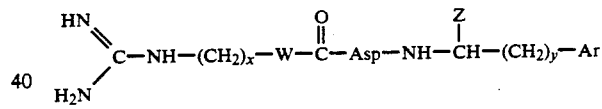

wherein
x=4 to 8,
y=0 to 4,
W=$CH_2$—$CH_2$ or CH=CH,
Z=H, COOH, $CONH_2$, $CH_2OH$, $CO_2R$, $CH_2OR$ or $C_{1-6}$ alkyl,
R=$C_{1-6}$ alkyl,
Ar=a nitrogen-containing heterocyclic group, and
Asp=aspartic acid residue.

The nitrogen-containing heterocyclic group is preferably selected from the group consisting of substituted or unsubstituted 5- or 6-membered heterocycles, purines, and 5- or 6-membered heterocycles fused to a benzene or tetrahydrobenzene ring.

The 5-membered heterocycle preferably is a pyrrole group, e.g. 2-(3-pyrrolyl)ethyl amide or 3-pyrrolyl alanine.

The 6-membered heterocycle preferably is a pyridyl group, e.g. 2-(4-pyridyl)ethyl amide, 3-(3-pyridyl)alanine, nicotinyl or nicotinamide; a pyrazine group, e.g. pyrazinamide; or a pyrimidinyl group, e.g. 2,4-diaminopyrimidine, 2-oxy-4-aminopyrimidine (cytosine), 2,4-dioxypyrimidine (uracil) or 2,4-dioxy-5-methylpyrimidine (thymine).

The purines are illustrated by 2,6-diaminopurine, 6-aminopurine (adenine), 2-amino-6-oxypurine (guanine), 1-methyl-guanine, $N^2$-dimethylguanine, hypoxanthine and 1-methyl-hypoxanithine.

The 5-membered heterocycle fused to a benzene or tetrahydrobenzene ring preferably is an indolyl group, e.g. 2-(3-indolyl)ethyl amide (tryptamine), 2-amino-3-indolylpropionic acid (tryptophan), or a tetrahydroindolyl group.

The 6-membered heterocycle fused to a benzene or tetrahydrobenzene ring preferably is a quinoline or quinoxaline derivative. These are illustrated by a quinolinyl group, e.g. 2-quinolinyl, an isoquinolinyl group, quinoxainyl or tetrahydroquinolinyl.

The nitrogen-containing heterocyclic group can be unsubstituted or substituted with, e.g. OH, $C_{1-6}$ alkyl, OR in which $R = C_{1-6}$ alkyl, amino, nitro or halo, e.g. Cl, Br or F. These substitutions can be on any available position on the ring. In a preferred group of the novel peptide mimetic compounds, $x = 5$ to 6. In the peptide mimetic compounds in which W is CH=CH, a trans double bond is preferred.

When compared structurally with the Arg-Gly-Asp-(O-methyl-Tyr)-$NH_2$ and other tetrapeptide derivatives of U.S. Pat. No. 4,857,508, it will be seen that in the present compounds a peptide bond

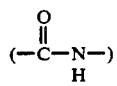

is replaced with a pseudopeptide or peptide mimetic bond (—$CH_2$—$CH_2$—) linked to an N-terminal guanidino group, and a nitrogen-containing heterocyclic group is at the C-terminus. Thus, in an illustrative preferred compound of the above group in which $x = 5$, $y = 1$, W=$CH_2$—$CH_2$, Z=COOH and Ar=3-indole, namely 8-guanidino-octanoyl-Asp-Trp, the amide bond between the N-terminal residue and the glycine residue is replaced with a pseudopeptide bond and a tryptophan residue is at the C-terminus.

The novel inhibitor compounds of this invention are more resistant to proteolysis than the prior inhibitors without the pseudopeptide bond and thus have longer duration of activity. These novel compounds are active inhibitors of platelet aggregation. In an in vivo thrombocytopenia assay, the preferred 8-guanidino-octanoyl-Asp-Trp was active at an effective dose of about 0.05 mg/kg of body weight.

DETAILED DESCRIPTION OF THE INVENTION

The novel platelet aggregation inhibitors of the present invention can be prepared by methods analogous to conventional peptide synthesis. Thus, suitable methods of synthesis are conventional solution phase peptide synthesis or the solid phase synthesis of Merrifield, *J. Amer. Chem. Soc.* 85, 2149–2154 (1963); *Science* 150, 178–185 (1965); *Ibid.* 232, 341–347 (1986).

The solid phase synthesis provides a growing peptide chain anchored by its carboxyl terminus to a solid support, e.g., a resin such as chloromethylated polystyrene resin or p-methylbenzhydrylamine resin when synthesizing a peptide amide derivative. The use of various N-protecting groups, e.g. the carbobenzoxy group (Cbz), the t-butyloxycarbonyl group (Boc) or the N-(9-fluorenyl-methylcarbonyl) group (Fmoc), various coupling reagents, e.g., dicyclohexylcarbodiimide (DCC), carbonyldiimidazole or disuccinimidyl carbonate (DSC), various cleavage reagents, e.g., trifluoroacetic acid (TFA) in methylene chloride ($CH_2Cl_2$) and other such reagents of classical solution phase peptide synthesis also are used in conventional solid phase synthesis of peptides.

In the present invention, aspartic acid can be used as the C-terminal moiety of the peptide mimetic compound for initiating the solid phase synthesis, and protection can be carried out with Fmoc blocking reagents. An illustrative solid phase resin is a Sasrin® resin which is commercially available from Bachem Biosciences, Philadelphia, Pa., and Sigma Chemical Co., St. Louis, Mo. The Fmoc-O-t-butyl-L-aspartic acid is amidated with a suitable aryl amine, for example, 4-pyridylethylamine and, following removal of the t-butyl group, the product is attached to the solid phase resin. In a succeeding step, the Fmoc group is removed from the aspartic acid residue and the Fmoc protected aminoalkanoyl group is coupled thereto. Following removal of the latter Fmoc group, the amino group is guanidated and the resin is then cleaved off to yield the desired peptide mimetic product.

The following schematic outline illustrates the foregoing solid phase synthesis of 8-guanidino-octanoyl-Asp-2-(4-pyridyl)-ethylamide.

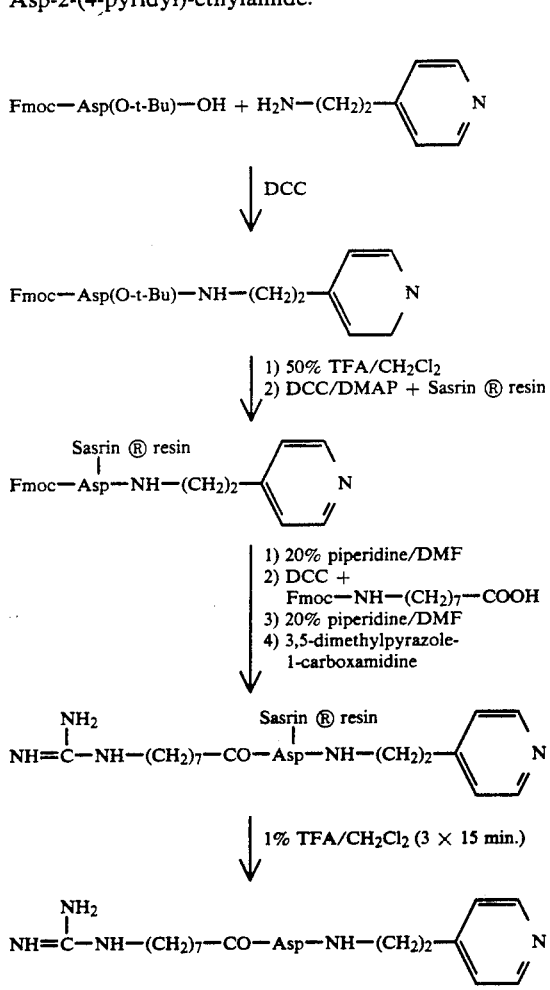

Another suitable method of synthesis of the platelet aggregation inhibitors of the present invention is a solution phase synthesis. This method can commence with the preparation of an aspartyl amide which is then coupled with a guanidino alkanoic acid as illustrated in the following schematic outline for the synthesis of 8-guanidino-octanoyl-Asp-2-(4-pyridyl)-ethyl amide.

ing the protecting group, is guanidated to the guanidino trans-2-alkenoic acid. The latter compound can then be

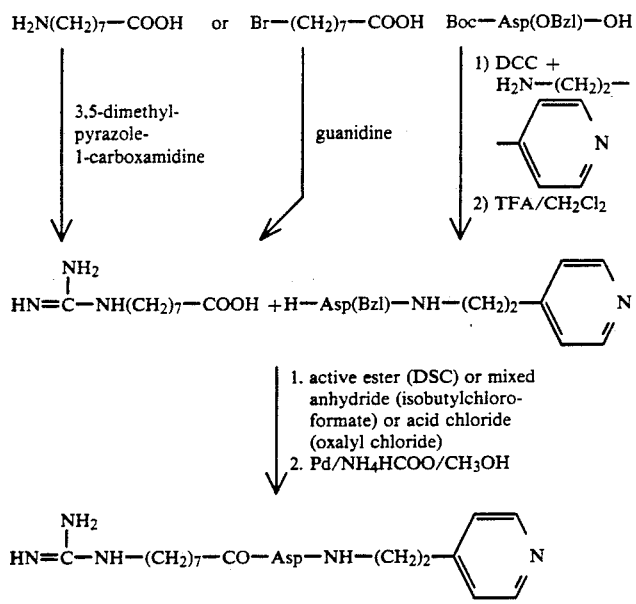

An alternate method of synthesis can be employed for providing a trans-double bond in the aliphatic chain whereby a guanidino trans-2-alkenoic acid is used as an intermediate instead of the guanidino alkanoic acid. In this synthesis, a suitable ω-amino alkanol, e.g. 6-amino-1-hexanol, is used as the starting material instead of an ω-amino alkanoic acid. After protecting the amino group, the amino alkanol is oxidized to an aldehyde, converted to the trans-2-alkenoic acid and, after removing the protecting group, is guanidated to the guanidino trans-2-alkenoic acid. The latter compound can then be used as an intermediate in place of the guanidino alkanoic acid in the foregoing schematic method or in the following schematic outline which shows the synthesis of the exemplary 8-guanidino-2E-octenoyl-Asp-Trp and its ethyl ester analog, 8-guanidino-2E-octenoyl-Asp-Trp(O-Et). In this reaction sequence the compound numbers correspond to the compound numbers in Examples VI to VIII hereinafter.

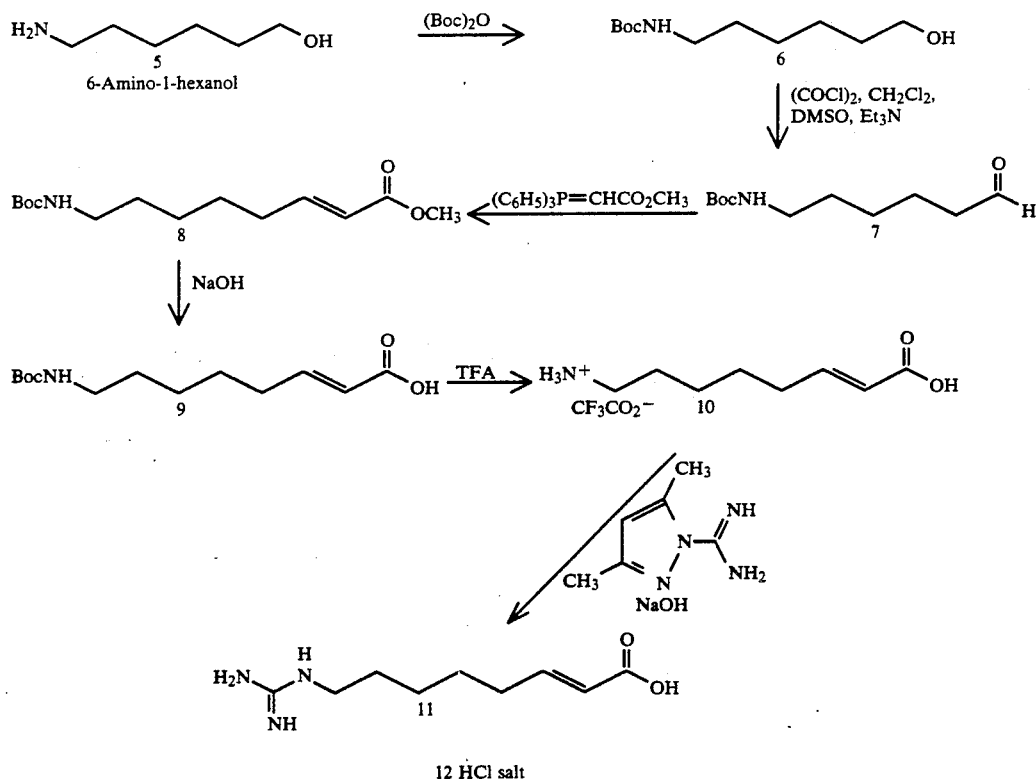

-continued

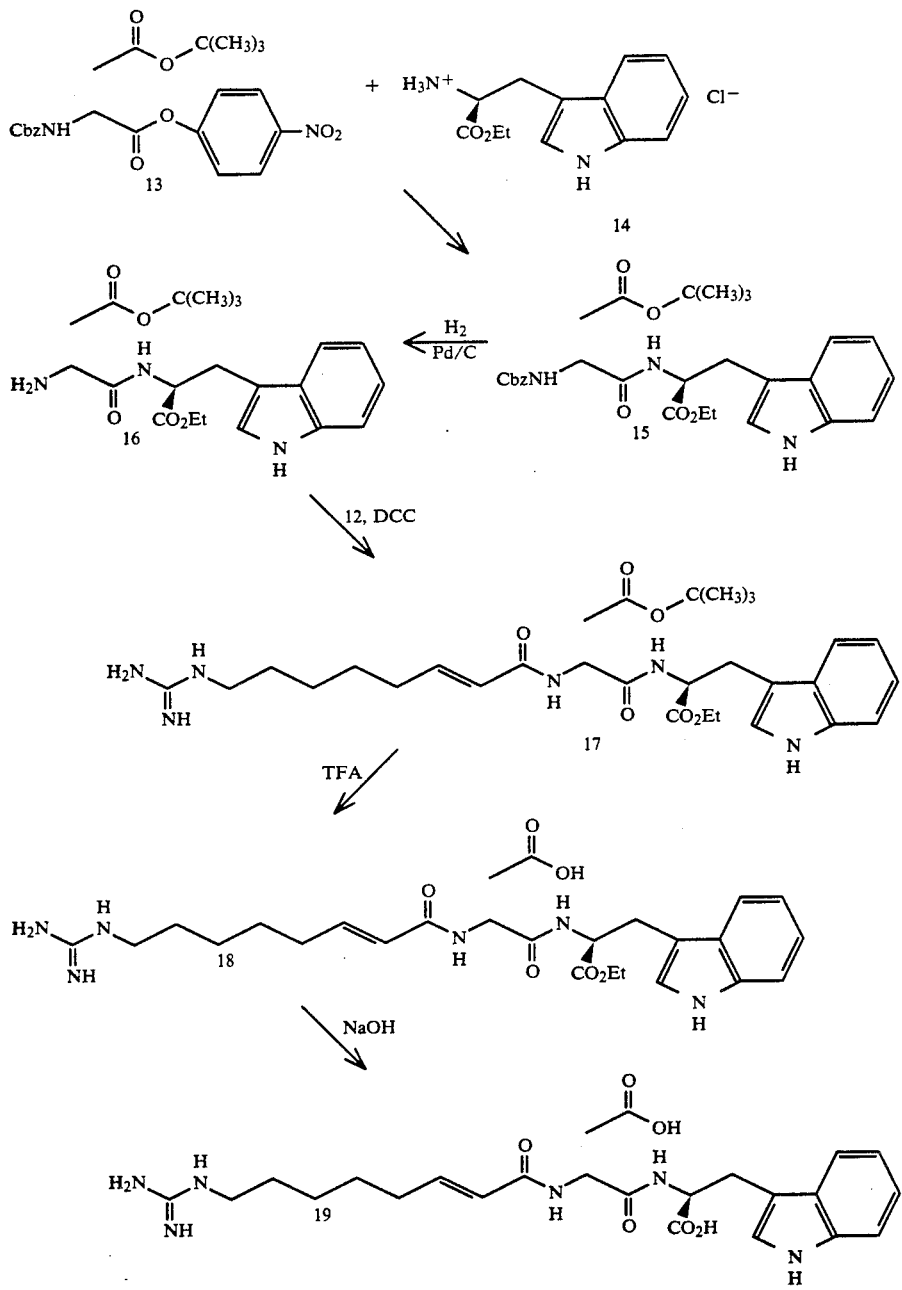

Although specific methods of making the peptide mimetic compounds are described herein, it will be understood that these novel compounds are not limited to the disclosed methods of making them.

The platelet-binding inhibitor activity of the peptide mimetic compounds of this invention can be demonstrated by various assays. In one assay, platelet aggregation is examined in platelet-rich plasma which also is rich in fibrinogen and other plasma proteins. The % inhibition is determined for the test compound by comparing the extent of platelet aggregation in the presence and absence of the test compound.

In another test, the inhibitory activity of the peptide mimetic compound on fibrinogen binding is determined in an assay essentially as described by Plow et al., Blood 70, 110–115 (1987). In this assay, the potency of the test compound ($IC_{50}$) is determined as the concentration of the compound required to inhibit 50% of $^{125}I$-fibrinogen binding.

In still another test, the effect of the peptide mimetic compound on collagen induced thrombocytopenia (platelet aggregation) is measured in vivo in the rat. Again, the % inhibition is determined for the test compound and compared against a saline or ethanol vehicle in the absence of the test compound.

In these assays, the test compound results are then compared with the activity of the known active inhibitor tetrapeptide Arg-Gly-Asp-Ser.

Based on the test results obtained with these compounds, it is believed that they will be useful in a variety of therapeutic interventions, for example, preventing re-occlusion following re-canalization procedures such as post fibrinolytic therapy, thrombolytic therapy, angioplasty and coronary bypass surgery. Other potential uses are for prevention of myocardial infarct, recurrent myocardial infarct, unstable angina, peripheral artery disease, cerebral ischemia, stroke and diseases of platelet hyperaggregability, and to prevent occlusion in hemodialysis, shunt procedures and to prevent progression of atherosclerosis.

The following examples will further illustrate the invention in greater detail although it will be appreciated that the invention is not limited to these specific examples.

EXAMPLE I

A. Synthesis of 8-guanidino-octanoic acid 3,5-dimethyl-pyrazole-1-carboxamidine (Aldrich) (100 g; 0.5 Mole) and N,N-diisopropylethyl amine (DIEA) (65 g; 0.5 Mole) were suspended in dioxane (300 ml) and water (115 ml). 8-Amino-octanoic acid (48 g; 0.3 Mole) was added to the mixture with stirring. The colorless solution was then refluxed for 2 days. The product was filtered and washed with water (3×50 ml).

The dried material weighed 60 g; FAB-MS: $(M+H)=202$.

B. Formation of free guanidine

Guanidine carbonate (11.41 g; 63.3 mmoles) was dissolved in 25 ml of water and sulfuric acid (3.52 ml; 63.3 mmoles) and barium hydroxide (19.97 g; 63.3 mmoles) were added. The mixture was stirred and cooled on ice. The precipitate was removed by filtration or centrifugation and the solution containing the free guanidine was used directly in the next step.

C. Synthesis of 9-guanidino-nonanoic acid

9-Bromo-nonanoic acid (5 gm; 21.1 mmoles) was dissolved in dioxane (50 ml) and the free guanidine solution from B was added. The mixture was refluxed overnight, and the white precipitate was filtered and washed three times with cold water and then lyophilized from one equivalent of 0.5M HCl. The yield was 2.77 g (85%) and the structure of the title compound was verified by FAB-MS, NMR, and elemental analysis.

EXAMPLE II

Synthesis of 8-guanidinooctanoyl-Asp-2-(3-indolyl)ethyl amide (1)

A. Asp-2-(3-indolyl)ethyl amide-TFA

Boc-Asp(t-Bu)-OH (Bachem Bioscience) (5 mmoles) and dicyclohexylcarbodimide (1.03 g, 5 mmoles) were dissolved in ethyl acetate/dimethylformamide (8:2; 50 ml). The reaction mixture was stirred for 30 minutes and 3-(2-aminoethyl)indole (0.8 g, 5 mmoles) was added dropwise. The coupling reaction was carried out overnight. The precipitate was filtered and the filtrate was evaporated to dryness. The oily residue was treated with 50% trifluoroacetic acid/methylene chloride (1:1; 50 ml) for 30 minutes. The reaction mixture was evaporated to dryness and the residue was used without any further purification.

B. 8-Guanidinooctanoyl-Asp-2-(3-indolyl)ethyl amide 8-guanidinooctanoic acid-HCl (2.5 g, 10 mmoles), disuccinimidyl carbonate (Fluka) (2.5 g, 10 mmoles) and 4-dimethylamino-pyridine (0.3 g) were dissolved in pyridine/dimethylformamide (1:3; 50 ml). The solution was stirred at room temperature overnight. In a separate flask, Asp-2-(3-indolyl)ethyl amide-TFA (A) was dissolved in dimethylformamide (15 ml) and neutralized with diisopropylethyl amine. Both solutions were combined and the mixture was stirred overnight. The reaction mixture was evaporated to dryness. The product was purified on a Waters reverse-phase $C_{18}$ μBondapak column (1.9 cm×15 cm) using a linear gradient of 5% to 40% acetonitrile/water/0.05% trifluoroacetic acid (30 minutes) with a flow rate of 9 ml/min. to give the title product (1) in an overall yield of 5%. The product purity and structure were verified by analytical HPLC (Vydac $C_{18}$-column, 0.46 cm×15 cm, using a linear gradient of 10–70% acetonitrile/water/0.05% TFA, 30 min, with a flow rate of 1.5 ml/min.), amino acid analysis and Fast atom bombardment mass spectrometry $(M+H=459)$.

EXAMPLE III

Synthesis of 8-guanidinooctanoyl-Asp-Trp (2)

8-guanidinooctanoic acid-HCl (0.73 g, 3.63 mmoles), disuccinimidyl carbonate (0.93 g, 3.63 mmoles) and 4-dimethylamino-pyridine (0.10 g, 0.82 mmoles) were dissolved in dimethylformamide/pyridine (9:1; 50 ml). The mixture was stirred at room temperature overnight. In a separate flask, Asp-Trp [Bachem Bioscience, Philadelphia, Pa.] (1.1 g, 3.45 mmoles) was dissolved in aqueous saturated sodium bicarbonate solution (10 ml). Both solutions were combined and allowed to react overnight at room temperature. The reaction mixture was evaporated to dryness, and the product purified on a Waters reverse-phase $C_{18}$ μBondapak column (1.9 cm×15 cm) using a linear gradient of 2% to 40% acetonitrile/water/0.05% trifluoroacetic acid over 20 minutes at a flow rate of 15 ml/min. to give the title product (2) in an overall yield of 16%. The product purity and structure were verified by analytical HPLC (Vydac $C_{18}$-column, 0.46 cm×15 cm, using a linear product of 15–45% acetonitrile/water/0.05% TFA, 20 min., amino acid analysis, proton NMR and Fast atom bombardment mass spectrometry $(M+H=503.3)$.

EXAMPLE IV

Synthesis of 8-guanidinooctanoyl-Asp-2-(4-pyridyl)ethyl amide (3)

A. Asp(t-Bu)-2-(4-pyridyl)ethyl amide

Fmoc-Asp(t-Bu)-OH (Bachem Bioscience) (9.04 g, 22 mmoles) and dicyclohexylcarbodiimide (4.12 g, 20 mmoles) were dissolved in dimethylformamide/methylene chloride (1:5; 50 ml) and cooled in an ice bath. The mixture was stirred for 15 minutes and 4-(2-aminoethyl)-pyridine (2.44 g, 20 mmoles) was added. The combined reaction mixture was stirred overnight and the precipitate was filtered. The filtrate was evaporated to dryness. The residue was redissolved in ethyl acetate (300 ml) and washed with saturated sodium bicarbonate solution (3 times), 0.5N HCl (2 times) and water. The organic layer was dried over sodium sulfate, filtered and the filtrate was evaporated to dryness. The residue was treated with 20% diethylamine/methylene chloride (50 ml) for 1.5 hours, and the reaction mixture was evaporated to dryness and used without further purification.

B. 8-Guanidinooctanoyl-Asp-2-(4-pyridyl)ethyl amide 8-guanidinooctanoic acid-HCl (0.94 g, 4 mmoles), disuccinimidyl carbonate (1.1 g, 4.4 mmoles) and 4-dimethylamino-pyridine (0.5 g) were dissolved in pyridine/dimethylformamide (1:5; 25 ml) and stirred for 2 hours. To this solution was added Asp-(t-Bu)-2-(4-pyridyl)ethyl amide (A) and the mixture was stirred overnight. The solvent was removed in vacuo and the residue was treated with 50% trifluoroacetic acid/methylene chloride (50 ml) for 30 minutes. The solid material was filtered and the filtrate was evaporated to dryness. The product was purified on a Waters $C_{18}$ μBondapak column (1.9 cm×15 cm) using a linear gradient of 5% to 45% acetonitrile/water/0.05% trifluoroacetic acid (30 min.) with a flow rate 9 ml/min. to give the title product (3) in an overall yield of 6%. The product purity and structure were verified by analytical HPLC (Vydac $C_{18}$-column, 0.46 cm×25 cm, using a linear gradient of 5–45% acetonitrile/water/0.05% TFA, 30 min., with a flow rate of 1.0 ml/min.), amino acid analysis and Fast atom bombardment mass spectrometry (M+H=421.8).

EXAMPLE V

Synthesis of 8-guanidinooctanoyl-Asp-3-(3-pyridyl)-alanine (4)

A. Asp-3-(3-pyridyl)alanine methyl ester-TFA

Boc-3-(3-pyridyl)alanine (Synthetech) (1 g; 3.76 mmoles) was dissolved in methanol (100 ml). The solution was cooled in an ice bath and bubbled with HCl gas for 1 hour with stirring. The reaction mixture was evaporated to dryness and the residue was triturated with ether. The solvent was removed in vacuo and the remaining ester was suspended in pyridine (30 ml). Diisopropylethylamine (0.65 g; 5 mmoles) and Boc-Asp(t-Bu)OSu (Bachem Bioscience) (OSu=succinimidyl ester) (1.8 g; 4.66 mmoles) in dimethylformamide (10 ml) were added consecutively with stirring. The clear solution was stirred at room temperature overnight. The reaction mixture was evaporated to dryness and the oily residue was then treated with 70% trifluoroacetic acid in dichloromethane (100 ml) for 1 hour. The solvent and acid were removed in vacuo. The remaining oil was dried over sodium hydroxide in vacuo. This material was used without any further purification.

B. 8-Guanidinooctanoyl-Asp-3-(3-pyridyl) alanine

8-Guanidinooctanoic acid hydrochloride (2.5 g; 10.6 mmoles), disuccinimidyl carbonate (2.5 g; 10 mmoles) and 4-dimethylaminopyridine (0.3 g) were dissolved in dimethylformamide/pyridine (150 ml; 2:1). The mixture was stirred at room temperature overnight. Crude Asp-3-(3-pyridyl)alanine methyl ester-TFA (A), diisopropylethylamine (0.65 g; 5 mmoles) and sodium bicarbonate (5 mmoles) in dimethylformamide/water (15 ml; 8:2) were added to the above solution. The reaction mixture was stirred overnight and the solvent was removed in vacuo. The residue was then dissolved in methanol (20 ml) and the solution (total volume of 40 ml) was cooled in an ice bath. Sodium hydroxide (2.5N; 40 ml) was added slowly with stirring. The mixture was stirred for another 4 hours at 0° C. and neutralized with 4N HCl. The solvent was removed in vacuo and the residue was purified on a $C_{18}$-μBondapak column (1.9 cm×15 cm) using a linear gradient of 3–25% acetonitrile/water over 30 minutes at a flow rate of 9 ml/min. to give the title product (4% in an overall yield of 12–15%. The product purity and structure were verified by analytical HPLC (Vydac $C_{18}$-column, 0.46 cm×15 cm, using a linear gradient of 2–35% acetonitrile/water/0.05% TFA, 20 min., with a flow rate of 1.5 ml/min), amino acid analysis and Fast atom bombardment mass spectrometry (M+H=464).

EXAMPLE 6

Synthesis of 8-guanidino-2E-octenoic acid hydrochloride (12)

A. N-Boc-6-amino-1-hexanol (6)

A solution of 50 g (0.43 mole) 6-amino-1-hexanol (5) in 350 mL methylene chloride was chilled in an ice bath to 5° C. and 98 mL (93.1 g, 0.43 mole) di-tert-butyl dicarbonate was added over 5 min. The ice bath was removed and the mixture was stirred at room temperature overnight. After removing the solvent in vacuo, the pale solid, mp 36°-37° C., amounted to 92.5 g of crude title compound (6).

B. N-Boc-6-aminohexanal (7)

To a stirred solution of 5.3 mL (7.71 g, 60.7 mmoles) oxalyl chloride in 100 mL methylene choride at −70° C. under argon was added 8.6 mL (10.23 g, 121.5 mmoles) dimethyl sulfoxide in 30 mL methylene chloride. After 2 min. a solution of 12 g (55.2 mmoles) of (6) in 50 mL methylene chloride was added over 5 min. After 20 min. 38.5 mL (27.9 g, 276 mmoles) triethylamine was added. After 10 min. more, the mixture was allowed to warm to 20° C. and 250 mL water was added. After separation, the aqueous layer was extracted again with methylene chloride and the combined organic layers were washed with brine and dried over sodium sulfate. After evaporation in vacuo, the residue was chromatographed (Flash, hexane-ethyl acetate, 7:3) to provide 11.36 g of a pale yellow oil (7).

C. Methyl N-Boc-8-amino-2E-octenoate (8)

A solution of 35.28 g (105.5 mmole) methyl (triphenylphosphoranylidene)acetate in 70 mL methylene chloride was added to a solution of 11.36 g (52.76 mmoles) of (7) in 20 mL methylene chloride. After 2 h at room temperature, the solution was concentrated in vacuo to remove most of the solvent and the residue was diluted with ether. The solid was removed by filtration and the filtrate was concentrated and the residue chromatographed (Flash, hexane-ethyl acetate 7:3). The product fraction amounted to 10.7 g of a colorless oil (8).

D. N-Boc-8-amino-2E-octenoic acid (9)

A solution of 10.7 g (39.4 mmoles) of (8) in 30 mL methanol was chilled in an ice bath and 59 mL of 1N sodium hydroxide was added. The ice bath was removed and the mixture was stirred at room temperature for 20 h. After evaporation of most of the methanol, the solution was acidified to pH 3 with 1N potassium bisulfate. The mixture was extracted with ether, and washed with water and brine. After drying over sodium sulfate and removal of solvent in vacuo, the residue was crystallized from ether-hexane to provide 9.55 g of the title compound (9), mp 76°-78° C. Anal. Calcd. for $C_{13}H_{23}NO_4$: C, 60.68; H, 9.01; N, 5.44. Found: C, 60.50; H, 9:00; N, 5.40.

E. 8-Amino-2E-octenoic acid trifluoroacetate salt (10)

A mixture of 45 mL trifluoroacetic acid and mL water was chilled in an ice bath while 34 g (0.132 mole) of (9) was added with stirring. The resulting solution was allowed to warm to room temperature over 1.5 h and then evaporated under a slow nitrogen stream overnight. The residue was triturated with ether. The solid was filtered, rinsed well with ether and dried to yield 21 g of the title compound (10), mp 77°–78° C. Anal. Calcd. for $C_{10}H_{15}NO_4F_3$: C, 44.28; H, 5.95; N, 5.16. Found: C, 4.07; H, 5.96; N, 5.09.

F. 8-Guanidino-2E-octenoic acid (11)

A suspension of 21 g (77.4 mmoles) of (10) and 31.1 g (155 mmoles) 3,5-dimethylpyrazole-1-carboxamidine nitrate in 50 mL dioxane, 2 mL water and 47.2 mL N,N-diisopropylethylamine was warmed on a steam bath until a clear solution was obtained. After stirring 20 h at room temperature, the solid was filtered and washed well with water to provide 13 g of crude title compound (11).

G. 8-Guanidino-2E-octenoic acid hydrochloride (12)

A suspension of 13 g (65 mmoles) of crude (11) in 75 mL 1N hydrochloric acid was warmed on a steam bath until a clear solution was obtained. After 1 h at room temperature crystals were noted. The mixture was chilled overnight and the crystals were filtered and dried to provide 13.86 g of title compound (12), mp 162° C. Anal. Calcd. for $C_9H_{18}N_3O_2Cl$: C, 45.86; H, 7.70; N, 17.83; Cl, 15.04. Found: C, 45.90; H, 7.64; N, 17.88; Cl, 14.79.

EXAMPLE VII

Synthesis of N-(8-guanidino-2E-octenoyl)-Asp-Trp(O-Et) (18)

A. N-Cbz-Asp(0-t-Bu)-Trp(O-Et) (15)

To a suspension of 5.52 g (12.4 mmole) of N-Cbz-Asp($\beta$-O-t-Bu)-$\alpha$-(p-nitrophenyl) ester (13) and 3.316 g (12.3 mmole) tryptophan ethyl ester hydrochloride (14) in 30 mL methylene chloride was added 1.5 mL (1.22 g, 12.3 mmoles) 1-methylpiperidine. The mixture was stirred at room temperature for 22 h. After evaporation of most of the solvent, the residue in ethyl acetate was washed with water and 5% sodium carbonate alternately until no more yellow color was noted. After washing with brine and drying over sodium sulfate, removal of solvent in vacuo left 6.30 g of the title compound (15).

B. Asp(O-t-but)-Trp(O-Et) (16)

A solution of 6.3 g (11.7 mmoles) of (15) in 100 mL tetrahydrofuran was hydrogenated over 1.4 g of 4% Pd/C at 5 psi hydrogen over a 20 h period. After removing the catalyst by filtration and evaporation of solvent the residue was chromatographed (Flash, hexane-ethyl acetate, 9:1–4:1). After recovery of 282 mg of reactant (15) the product fraction amounted to 4.18 g of the title compound (16).

C. 8-Guanidino-2E-octenoyl-Asp(O-t-Bu)-Trp(O-Et) (17)

To a solution of 2.49 g (10.5 mmoles) of (12) in 35 mL dimethylformamide at 0° C. was added 2.29 g (11 mmoles) N,N-dicylohexylcarbodiimide, followed immediately by 4.18 g (10.4 mmoles) of (16). The mixture was stirred for 24 h. The solids were removed by filtration and the filtrate was evaporated under a slow nitrogen stream. The residue in 20 mL methanol was diluted with 20 mL water. After chilling in an ice bath the small amount of solid was removed by filtration, the filtrate was evaporated and the residue was chromatographed on a 25 mm×1,000 mm PLC-20 column with YMC ODS-AQ 50$\mu$ spherical adsorbent developing with a gradient from water to methanol. The product fraction amounted to 5.75 g of the title product (17).

D. 8-Guanidino-2E-octenoyl-Asp-Trp(O-Et) (18)

To 1.85 g of crude (17) was added a mixture of 4 mL trifluoroacetic acid, 1.5 mL anisole, and 1 mL water. After stirring 1 hour at room temperature the mixture was allowed to evaporate under a slow nitrogen stream. Chromatography on a 25 mm×1,000 mm PLC-20 column with Partisil ODS-3, 40$\mu$ adsorbent developing with methanol/water/acetic acid (45:55:0.5) produced a product fraction which was lyophilized to provide 420 mg of the title product (18). Anal. Calcd. for $C_{26}H_{36}N_6O_6 \cdot 0.7\ CH_3CO_2H \cdot 0.6\ H_2O (C_{27.4}H_{40}N_6O_8)$: C, 56.60; H, 6.93; N, 14.45. Found: C, 56.86; H, 6.77; N, 14.56.

EXAMPLE VIII

Synthesis of 8-Guanidino-2E-octenoyl-Asp-Trp (19)

To a solution of 138 mg (18) in 0.5 mL methanol was added 0.5 mL of 1N sodium hydroxide with stirring. The solution was evaporated to a small volume under a nitrogen stream and then diluted to about 2 mL. After being stirred at room temperatures overnight, the solution was lyophilized. Chromatography on a 25 mm×1,000 mm PLC-40 column with YMC ODS-AQ, 50 $\mu$ spherical adsorbent developing with a water/acetic acid (99.5:0.5) to methanol/acetic acid (99.5:0.5) gradient produced a product fraction which was lyophilized to provide 103 mg of the title product (19). Anal. Calcd. for $C_{22}H_{31}N_5O_6 \cdot H_2O\ (C_{22}H_{33}N_5O_7)$: C, 55.10; H, 6.94; N, 14.60. Found: C, 54.73; H, 6.92; N, 14.88.

Other illustrative peptide mimetic compounds of the invention as defined herein can be prepared by methods analogous to the methods of Examples I to VIII, above, by substituting other suitable $\omega$-amino alkanoic acids, e.g., 7-aminoheptanoic acid or 10-aminodecanoic acid for an equivalent amount of the 8-aminooctanoic acid, or by substituting other suitable $\omega$-bromo alkanoic acids, e.g., 7-bromoheptanoic or 8-bromooctanoic acid for an equivalent amount of the 9-bromo nonanoic acid, or by substituting other $\omega$-amino alkanols, e.g., 5-amino-1-pentanol for an equivalent amount of the 6-amino-1-hexanol, and/or by substituting other suitable nitrogen-containing heterocyclic alkylamines or amino acids for an equivalent amount of any of the 3-(2-aminoethyl)imidole, tryptophan, 4-(2-aminoethyl)-pyridine or 3-(3-pyridyl)-alanine reactants in said Examples. Thus, tryptamine can be substituted in these examples by aryl alkyl amines such as, e.g., 3-(2-aminoethyl)quinoline, 2-(2-aminoethyl)quinoxaline, 2-(3-aminopropyl)pyrazine, 4-(aminomethyl)-pyridazine or 3-(ethyl)indoline and the like compounds, all of which are readily available from commercial and other such sources. Likewise, tryptophan can be substituted in these examples by amino acids such as, e.g., 2-, 4-, or 5-indolyl alanine, 3-quinolinyl alanine, 2-quinoxalinyl alanine or tetrahydro indolyl alanine and the like compounds, all of which can be readily prepared from the aryl aldehydes by the conventional general procedure of Folkers et al., *Int. J. Peptide & Protein Res.* 24, 197–200 (1984). So also, substitutions can be made with 1-thyminyl alanine, 1-uracil alanine and 2-purinyl alanine, which can be prepared by conventional general procedures as described by Kraas et al., *Chem. Ber.* 108, 1111–1117 (1975); Tjoeng et al., *Chem. Ber.* 109, 2615–2621 (1976). These illustrative peptide mimetic compounds are then tested in vitro for inhibition of fibrinogen binding and ADP induced platelet aggregation in human platelet rich plasma, and in vivo for inhibition of collagen induced rat thrombocytopenia. Test results of various of the foregoing illustrative test compounds are set forth in Table I following Example IX.

EXAMPLE IX

A. Fibrinogen Binding Assay

Fibrinogen binding was performed essentially as described by Plow et al., *Blood* 70, 110–115 (1987). Briefly, blood from human volunteers who had not taken any antiplatelet drugs in the previous two weeks was collected into 1/10th volume of CCD buffer (100 mM sodium citrates, 136 mM glucose, pH 6.5). The blood was centrifuged for 3 min at 1,000×g and platelet rich plasma was transferred to a plastic tube with a plastic pipet and placed on ice. After 15 minutes, ½ volume of ice cold CCD buffer was added and the sample was centrifuged at 900×g for 10 min at 2° C. The supernatant was decanted and the platelet pellet was gently resuspended in ½ the original volume of ice cold modified Tyrode's buffer (137 mM NaCl, 2.6 mM KCl, 12 mM NaHCO$_3$, 5.5 mM glucose, 15 mM HEPES, 0.5% BSA, pH 7.4). After incubating for 30 minutes at 37° C., the platelet count was adjusted to $4 \times 10^8$ platelets/ml with modified Tyrode's buffer To platelet samples ($1 \times 10^8$ platelets/ml) were added in sequence: ADP (10 μM), CaCl$_2$ (1 mM), test compound, and $^{125}$I-fibrinogen (0.3 μM) to the aforesaid final concentrations in a volume of 200 μl. The samples were incubated for 40 min at 37° C. and 50 μl aliquots were centrifuged at 8,000×g through a 20% sucrose pad (400 μl). The tubes were quick frozen and the tips containing the platelet pellet were cut and assayed for bound $^{125}$I-fibrinogen by gamma scintillation counting. Specific binding was determined in each test by subtracting from the total binding the amount of $^{125}$I-fibrinogen bound in the presence of a 60-fold excess of unlabeled fibrinogen. The potency of test compounds (IC$_{50}$) was determined as the concentration of compound required to inhibit 50% of $^{125}$I-fibrinogen binding.

B. In-Vitro Human Platelet Aggregation in PRP

Healthy male or female donors who had not taken any antiplatelet drugs for at least 2 weeks were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 100×g for 10 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of $2-3 \times 10^8$ platelets per ml. 400 μl of the PRP preparation and 50 μl of the compound to be tested or saline were preincubated for 1 minute at 37° C. in a Payton aggregometer (Payton Scientific, Inc., Buffalo, N.Y.). 50 μl of adenosine 5'diphosphate (ADP) (50 μM) was added to the cuvettes and the aggregation was monitored for 1 minute. All compounds are tested in duplicate. Results are calculated as follows: Percent of control = [(maximal OD minus initial OD of compound) divided by (maximal OD minus initial OD of control saline)] × 100. The % inhibition = 100 − (percent of control).

The compounds tested and their median inhibitory concentrations (IC$_{50}$) were as recorded in Table I. IC$_{50}$'s (if a compound showed 50% inhibition) were calculated by linear regression of the dose response curve.

C. In Vivo Rat Thrombocytopenia

Male rats [Charles River, CRL:CD(SD), 400–450 g] were used. The rats were anesthetized with Na pentabarbital (65 mg/kg, Vet Labs, Limited, Inc., Lenexa, Kan). Two incisions were made to expose both jugular veins. Using an infusion pump (Harvard Apparatus, South Natick, Mass.) and a 5 cc syringe with a 19 g. butterfly, the test compound or vehicle was infused into the left jugular vein at a rate of 0.39 ml/min for 3 min. After 2 min of compound/vehicle infusion, collagen (60 μg/kg) (Helena Laboratories, Beaumont, Tex.) was injected with a one ml syringe into the right jugular vein. The body cavity was opened and the vena cava was exposed for blood sampling. One min after the collagen injection, compound infusion was stopped and blood was sampled from the vena cava (within 30 sec) with a 3 cc syringe containing 0.3 mg of 4.5% EDTA/Tris (0.1M) (pH 7.35) plus 150 μM indomethacin. Platelet rich plasma (PRP) was prepared by centrifuging the blood at 126×g for 10 min. Five μl of PRP was counted in 20 ml of Isoton® III in a Coulter Counter.

Percent inhibition of collagen induced aggregation was calculated by comparison of the platelet counts in animals that were treated with test compound and collagen (a) with platelet counts for animals receiving no collagen (non-aggregated control) and (b) with platelet counts for animals receiving vehicle and collagen (aggregated control). ED$_{50}$s were calculated for the intravenously administered (i.v.) test compounds 1 to 4 and for compounds 2 and 4 which also were administered by gavage (i.g.) in saline.

The assay results for compounds 1 to 4 in Examples II to V, respectively, are set forth in Table I, below

TABLE I

| Compound | Binding IC$_{50}$ (M) | Platelet Aggregation IC$_{50}$ (M) | Rat Thrombocytopenia ED$_{50}$ (mg/kg) | |
|---|---|---|---|---|
| | | | i.v. | i.g. |
| 1 | $2.2 \times 10^{-6}$ | $5.0 \times 10^{-6}$ | 0.47 | N.D. |
| 2 | $2.5 \times 10^{-7}$ | $8.5 \times 10^{-7}$ | 0.05 | 0.13 |
| 3 | not done | $2.4 \times 10^{-5}$ | 0.06 | N.D. |
| 4 | $1.3 \times 10^{-6}$ | N.D. | 0.14 | ** |
| 18 | $6.0 \times 10^{-6}$ | N.D. | N.D. | N.D. |
| 19 | $6.0 \times 10^{-7}$ | N.D. | N.D. | N.D. |

TABLE I-continued

| Compound | Binding IC$_{50}$ (M) | Platelet Aggregation IC$_{50}$ (M) | Rat Thrombocytopenia ED$_{50}$ (mg/kg) i.v. | i.g. |
|---|---|---|---|---|
| RGDS* | $5 \times 10^{-5}$ | $1 \times 10^{-4}$ | * | |

*This standard peptide used as a control showed only 30% inhibition at the highest dose tested (10 mg/kg).
**16% inhibition at an oral dose of 5 mg/kg.
N.D. = Not Done.

The novel peptide mimetic compounds of this invention can be used for administration to humans and other mammals by conventional means, such as by parenteral or oral methods of administration, preferably in formulations with pharmaceutically acceptable diluents or carriers. An illustrative route of administration as a platelet aggregation inhibitor is parenteral, especially intravenously. Intravenous administration of the peptide mimetic compounds in solution with normal physiological saline, human albumin and other such diluents and carriers is illustrative. Orally, the peptide mimetic compounds of this invention can be administered in the form of tablets, powders, capsules, elixers and the like dosage forms in admixture with common solid and liquid diluents, carriers, suspending agents and adjuvants such as for example, cornstarch, lactose, talc, stearic acid, magnesium stearate, gelatin acacia and locust bean gums, alcohol, water, saline, dimethylsulfoxide (DMSO), vegetable oils and the like materials. Other suitable formulations of the active peptide mimetic compounds in pharmaceutically acceptable diluents and carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such examples be included within the scope of the appended claims.

What is claimed is:

1. A peptide mimetic compound having the following chemical structure:

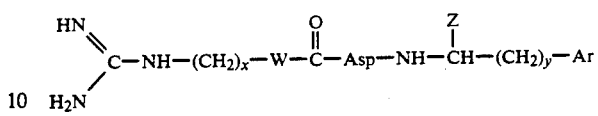

wherein
x = 4 to 8,
y = 0 to 4,
W = CH$_2$—CH$_2$ or CH=CH,
Z = H, COOH, CONH$_2$, CH$_2$OH, CO$_2$R, CH$_2$OR or C$_{1-6}$ alkyl,
R = C$_{1-6}$ alkyl,
Ar = a pyridyl group, and
Asp = aspartic acid residue.

2. A peptide mimetic compound of claim 1 in which the pyridyl group is 2-(4-pyridyl)ethyl amide.

3. A peptide mimetic compound of claim 1 in which the pyridyl group is 3-(3-pyridyl)alanine.

4. 8-Guanidinooctanoyl-Asp-2-(4-pyridyl)ethyl amide.

5. 8-Guanidinooctanoyl-Asp-3-(3-pyridyl)alanine.

6. The method of inhibiting platelet aggregation in a warm blooded mammal comprising administering to said mammal an effective amount of a peptide mimetic compound of claim 1 in a pharmaceutically acceptable carrier.

7. The method of inhibiting formation of a thrombus in a warm blooded mammal comprising administering to said mammal an effective amount of a peptide mimetic compound of claim 1 in a pharmaceutically acceptable carrier.

8. A pharmaceutical composition which comprises a peptide mimetic compound of claim 1 in an amount effective for inhibiting platelet aggregation with a pharmaceutically acceptable carrier.

* * * * *

UNITED STATES PATENT AND TRADEMARK OFFICE
CERTIFICATE OF CORRECTION

PATENT NO. : 5,091,396

DATED : Feb. 25, 1992

INVENTOR(S) : Foe S. Tjoeng, Steven P. Adams, Robert B. Garland and Masateru Miyano It is certified that error appears in the above-identified patent and that said Letters Patent is hereby corrected as shown below:

At cols. 7-8, in each of compound numbers 13, 15, 16, 17, 18 and 19, the dangling group at the top of the structure should be connected at its left end carbon to the lower chain structure with a perpindicular carbon to carbon single bond. In the abstract, sixth line from the bottom, "C=CH" should read --CH=CH--. In col. 12, line 3, "(4%" should read --(4)--.

Signed and Sealed this

Third Day of August, 1993

Attest:

MICHAEL K. KIRK

*Attesting Officer*     Acting Commissioner of Patents and Trademarks